(12) United States Patent
Mehta et al.

(10) Patent No.: US 9,180,124 B2
(45) Date of Patent: Nov. 10, 2015

(54) NICOTINE CONTAINING FORMULATION

(75) Inventors: Bharat Pravinchandra Mehta, Mumbai (IN); Rajen Dhirubhai Shah, Pune (IN); Manoj Kantilal Patel, Thane (IN); Parmeshwar B. Bang, Vapi (IN)

(73) Assignee: J. B. Chemicals and Pharmaceuticals Limited, Mumbai (IN)

( * ) Notice: Subject to any disclaimer, the term of this patent is extended or adjusted under 35 U.S.C. 154(b) by 0 days.

(21) Appl. No.: 13/513,463

(22) PCT Filed: Dec. 1, 2010

(86) PCT No.: PCT/IN2010/000775
§ 371 (c)(1),
(2), (4) Date: Jun. 1, 2012

(87) PCT Pub. No.: WO2012/035541
PCT Pub. Date: Mar. 22, 2012

(65) Prior Publication Data
US 2012/0244104 A1    Sep. 27, 2012

(30) Foreign Application Priority Data
Sep. 16, 2010    (IN) .......................... 2564/MUM/2010

(51) Int. Cl.
*A61K 31/465*    (2006.01)
(52) U.S. Cl.
CPC .................................... *A61K 31/465* (2013.01)
(58) Field of Classification Search
None
See application file for complete search history.

(56) References Cited

U.S. PATENT DOCUMENTS

| 4,806,356 | A |   | 2/1989 | Shaw |
|---|---|---|---|---|
| 4,967,773 | A |   | 11/1990 | Shaw |
| 5,110,605 | A |   | 5/1992 | Acharya |
| 5,362,496 | A |   | 11/1994 | Baker et al. |
| 5,549,906 | A |   | 8/1996 | Santus |
| 5,593,684 | A |   | 1/1997 | Baker et al. |
| 5,721,257 | A |   | 2/1998 | Baker et al. |
| 6,110,495 | A | * | 8/2000 | Dam ............................ 424/464 |
| 6,183,775 | B1 |   | 2/2001 | Ventouras |
| 6,280,761 | B1 |   | 8/2001 | Santus |
| 2004/0107971 | A1 |   | 6/2004 | De |
| 2004/0191322 | A1 | * | 9/2004 | Hansson ....................... 424/489 |
| 2006/0171994 | A1 |   | 8/2006 | Dupinay et al. |
| 2009/0087486 | A1 |   | 4/2009 | Krumme |
| 2009/0214442 | A1 |   | 8/2009 | Agarwal et al. |
| 2010/0124560 | A1 |   | 5/2010 | Hugerth et al. |

FOREIGN PATENT DOCUMENTS

| DE | 102005058569 A1 | 6/2007 |
|---|---|---|
| WO | WO-02076211 A1 | 10/2002 |
| WO | WO-2007104675 A1 | 9/2007 |
| WO | WO-2009134947 A1 | 11/2009 |

OTHER PUBLICATIONS

Michaud, "Pharmaceutical Confectionary", Pharmaceuticals, pp. 1-4, 2002.*

(Continued)

*Primary Examiner* — Ernst V Arnold
*Assistant Examiner* — Kyung Sook Chang
(74) *Attorney, Agent, or Firm* — Blank Rome LLP

(57) ABSTRACT

Disclosed is nicotine containing solid oral transmucosal dosage forms containing a therapeutically effective amount of nicotine polacrilex, citric acid monohydrate, sucrose and liquid glucose. The dosage form is preferably in the form of lozenge.

8 Claims, 1 Drawing Sheet

(56) References Cited

OTHER PUBLICATIONS

Maheshwari et al. "A review on lozenges", Journal of British Biomedical Bulletin (BBB), pp. 35-43 (2013).*

International Search Report issued in PCT/IN10/00775 on Sep. 28, 2011.
Supplementary European Search Report issued in EP10857212 on Mar. 21, 2013.

* cited by examiner

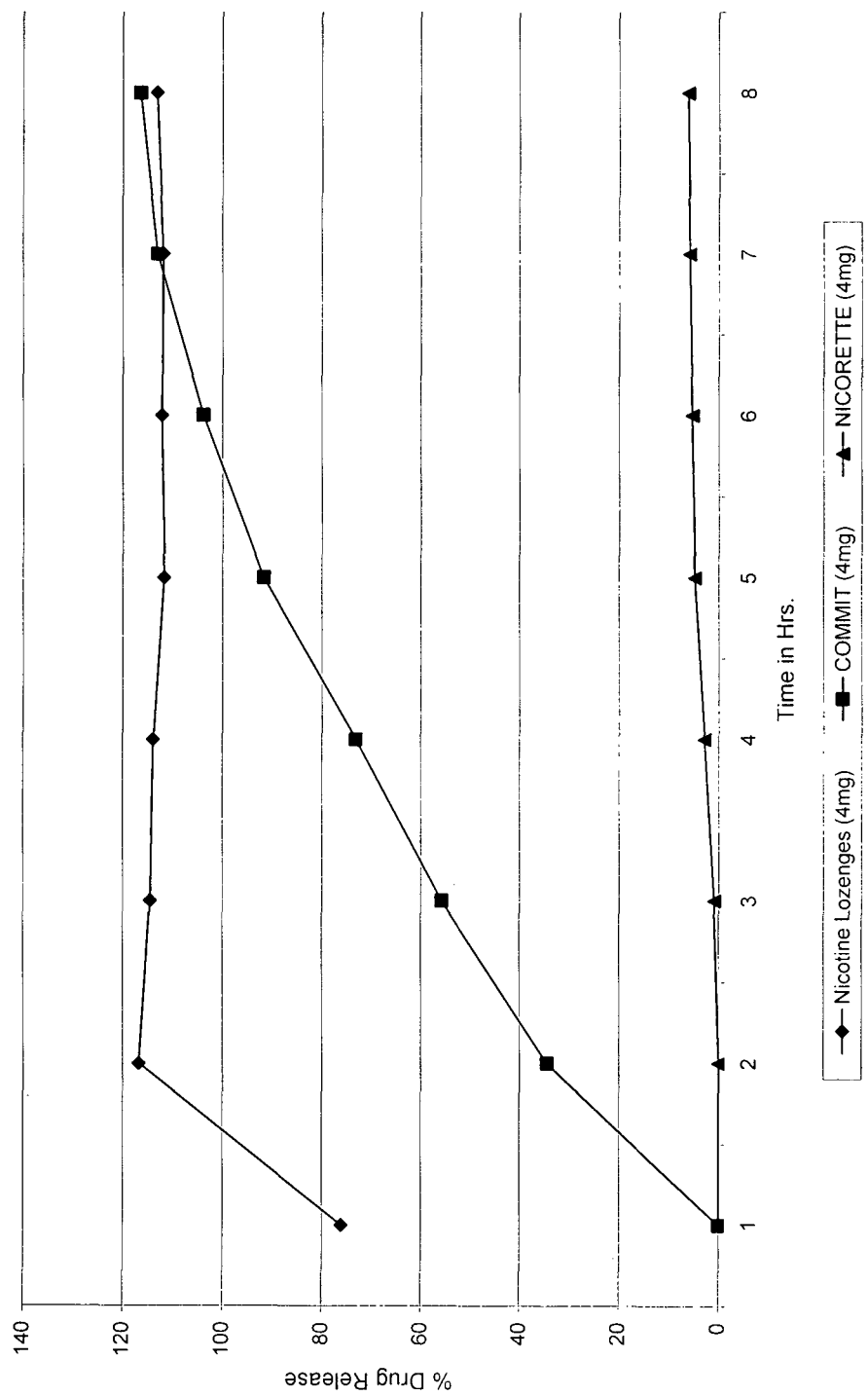

NICOTINE CONTAINING FORMULATION

This application is a U.S. National Stage Application of International Application No. PCT/IN2010/000775, filed Dec. 1, 2010, which claims priority to Indian Patent Application No. 2564/MUM/2010, filed Sep. 16, 2010, the contents of which are hereby incorporated by reference.

FIELD OF THE INVENTION

The present invention in general relates to the field of nicotine replacement therapy (NRT). More particularly, the invention relates to solid oral transmucosal nicotine dosage forms to deliver therapeutically effective amount of nicotine or nicotine derivatives to a patient in need of nicotine replacement therapy.

RELEVANT ART

Nicotine ((S)-3-(1-methyl-2-pyrrolidinyl)pyridine) is an alkaloid found in plants (Solanaceae), predominantly in tobacco and coca, and in lower quantities in tomato, potato, eggplant, and green pepper. Nicotine is a hygroscopic, oily, colorless or pale yellow liquid, which is miscible with water in its base form. As a nitrogenous base, nicotine forms salts with acids, which are usually solid and water soluble. Nicotine and its derivatives are readily absorbed from the gastrointestinal tract, the buccal mucosa, the respiratory tract, and intact skin, and widely distributed throughout the tissues. Therapeutically, nicotine and its derivatives are used in Nicotine Replacement Therapy for smoking cessation.

Nicotine replacement therapy (NRT) relieves withdrawal symptoms, significantly improving smoking cessation rates. Various nicotine replacement therapy products such as chewing gums, lozenges and transdermal patches are well popular forms known and available commercially. Lozenges and chewing gums provide oral delivery of nicotine, whereas transdermal patches treatments delivery nicotine through the patient's skin. Examples of oral lozenges are found in number of publications, including but not limited to U.S. Pat. Nos. 4,806,356 and 4,967,773 to Shaw; U.S. Pat. No. 5,110,605 to Acharya et al.; U.S. Pat. Nos. 5,549,906 and 6,280,761 to Santus; U.S. Pat. No. 6,183,775 to Ventouras; US Publication 20090214442 to Rajendra et al.; WO Publication 2007104675 to Axelsson et al. and WO Publication 2009134947 to Chen. Also, U.S. Pat. Nos. 5,593,684; 5,721, 257 and 5,362,496 (all to Baker et al.) disclose methods and therapeutic uses for smoking cessation, utilizing both transdermal nicotine delivery for obtaining base-line nicotine plasma levels, and transmucosal administration of nicotine to satisfy transient cravings. While such means are useful to help reduce or quit smoking, there is an ongoing need to provide improved solid oral transmucosal dosage forms effective in nicotine cessation.

SUMMARY OF THE INVENTION

In one aspect of the present invention, there is provided a solid oral transmucosal dosage forms containing a therapeutically effective amount of nicotine or nicotine derivative useful in relieving nicotine withdrawal symptoms. The composition also includes inactive ingredients citric acid monohydrate, sucrose, liquid glucose, a pharmaceutically acceptable flavoring agent, and a pharmaceutically acceptable coloring agent.

In other aspect of the present invention, there is provided nicotine lozenges designed to be held in the patient's mouth and sucked to release nicotine into the buccal cavity. The lozenges contain a therapeutically effective amount of nicotine or nicotine derivative, preferably less than 5 mg, and most preferably from 1 mg to 4 mg nicotine.

In another aspect of the present invention, there is provided a method for preparing nicotine lozenges containing a therapeutically effective amount of nicotine or nicotine derivative, preferably less than 5 mg, and most preferably from 1 mg to 4 mg nicotine.

BRIEF DESCRIPTION OF DRAWINGS

The following figures illustrate the present disclosure, and none are intended to imply a necessary limitation.

FIG. 1 is a chart showing comparative dissolution profile for nicotine lozenges described in Example 2 of the present invention with traditional COMMIT lozenges (4 mg) and traditional NICORETTE chewing gums (4 mg).

DETAILED DESCRIPTION OF THE INVENTION

The present invention may comprise, consist of, or consist essentially of the components set forth below, unless otherwise stated.

Unless otherwise stated, the following terms used in the specification and claims having the meanings given below:

"A" or "an" includes one or more of the components.

"Buccal administration" or "transmucosal delivery" refers to any system or device used for oral administration of a drug to a patient that is held in the mouth and is used to deliver a drug through the buccal mucosa and into the patient's body. The term includes, but is not limited to, lozenges, capsules, and tablets.

"Nicotine" or "nicotine derivative" may be used interchangeably and refers to include nicotine free base, any pharmaceutically acid addition acceptable salt or metal salt of nicotine, derivatives of nicotine, nicotine complexes, tobacco extract or leaf, any compounds that produce a similar physiological effect as nicotine, such as lobeline. Preferable "nicotine" or "nicotine derivative" for use herein include, but are not limited to, nicotine monotartrate, nicotine bitartrate, nicotine hydrochloride, nicotine dihydrochloride, nicotine sulfate, nicotine zinc chloride monohydrate, nicotine salicylate, nicotine oil, nicotine complexed with cyclodextrin, polymer resins such as nicotine polacrilex, nicotine resinate, and mixtures thereof. The most preferable is nicotine polacrilex.

"Lozenge" refers to any lozenge, capsule, tablet, hard boiled candies, lollipops, or other device for transmucosal delivery of nicotine to a patient for relieving nicotine withdrawal symptoms.

In the formulations of the present invention, the dosage form comprises a therapeutically effective amount of nicotine, preferably nicotine polacrilex along with citric acid monohydrate, sucrose and liquid glucose. The formulation also contains a pharmaceutically acceptable coloring agent and a pharmaceutically acceptable flavoring agent. The coloring agent used is Color BQ Supra and flavoring agent used is Mentha Piperita.

In a preferred formulation of the present invention, the dosage form is a solid oral transmucosal dosage form. The solid oral transmucosal dosage form preferably is lozenge useful for buccal administration to a patient. In a most preferred formulation, the lozenge will contain a therapeutically effective amount of nicotine polacrilex, sucrose, liquid glucose, citric acid monohydrate, color BQ supra and mentha piperita.

Lozenges of the present invention are useful in relieving nicotine withdrawal symptoms, and as a means to reduce or stop tobacco use. The formulations may be used as a total or partial replacement of tobacco, and may be used concurrently with tobacco as part of a planned tobacco reduction program. A patient may consume a lozenge of the present invention at regular intervals throughout the day as part of a tobacco quit regime, or alternatively consume lozenge of the present invention intermittently in response to an acute nicotine craving.

The formulations of the present invention may also be administrated nasally in the form of nasal sprays.

Lozenges of the present invention are intended to deliver a therapeutically effective amount of nicotine or nicotine derivative, preferably less than 5 mg of nicotine, and, most preferably from 1 mg to 4 mg of nicotine.

Lozenges of the present invention may be packaged in such a manner as to aid in maintaining nicotine stability. Preferred packaging methods include strip pack, blister pack, aluminum film, pillow pouch, twist pack, container pack, or cigarette equivalent pack.

In order that the invention described herein can be more fully understood, the following examples are set forth. It should be understood that these examples are for illustrative purposes only, and are not to be construed as limiting the invention in any matter.

Example 1

Manufacturing Formula for Nicotine Lozenges 2 mg (with Liquid Glucose)

| Ingredients | mg/tablet |
| --- | --- |
| Nicotine Polacrilex (20%) | 10.0 |
| Equivalent to Nicotine | 2.0 |
| Citric Acid Monohydrate | 20.0 |
| Sucrose | 1597.0 |
| Liquid Glucose | 1024.0 |
| Flavor Mentha Piperita | 2.50 |
| Color BQ Supra | 0.020 |
| Purified Water | q.s. |

Manufacturing Process

Nicotine polacrilex, flavoring solution, coloring solution and Citric acid solution were mixed with syrup preparation in mixing screw to obtain solid mass. The solid mass was passed through rope sizer and batch former to get lozenges. The lozenges were packed into strip pack/blister pack.

Example 2

Manufacturing Formula for Nicotine Lozenges 4 mg (with Liquid Glucose)

| Ingredients | mg/tablet |
| --- | --- |
| Nicotine Polacrilex (20%) | 20.0 |
| Equivalent to Nicotine | 4.0 |
| Citric Acid Monohydrate | 20.0 |
| Sucrose | 1590.0 |
| Liquid Glucose | 1020.0 |
| Flavor Mentha Piperita | 2.50 |
| Color BQ Supra | 0.040 |
| Purified Water | q.s. |

Manufacturing Process

Nicotine polacrilex, flavoring solution, coloring solution and Citric acid solution were mixed with syrup preparation in mixing screw to obtain solid mass. The solid mass was passed through rope sizer and batch former to get lozenges. The lozenges were packed into strip pack/blister pack.

Example 3

Manufacturing Formula for Nicotine Lozenges 2 mg (with Isomalt)

| Ingredients | mg/tablet |
| --- | --- |
| Nicotine Polacrilex (20%) | 10.0 |
| Equivalent to Nicotine | 2.0 |
| Citric Acid Monohydrate | 20.0 |
| Isomalt | 2461.98 |
| Aspartame | 2.75 |
| Acesulfame Potassium | 2.75 |
| Flavor Mentha Piperita | 2.50 |
| Color BQ Supra | 0.020 |
| Purified Water | q.s. |

Manufacturing Process

Nicotine polacrilex, flavoring solution, coloring solution and Critic acid solution were mixed with syrup preparation in mixing screw to obtain solid mass. The solid mass was passed through rope sizer and batch former to get lozenges. The lozenges were packed into strip pack/blister pack.

Example 4

Manufacturing Formula for Nicotine Lozenges 4 mg (with Isomalt)

| Ingredients | mg/tablet |
| --- | --- |
| Nicotine Polacrilex (20%) | 20.0 |
| Equivalent to Nicotine | 4.0 |
| Citric Acid Monohydrate | 20.0 |
| Isomalt | 2451.96 |
| Aspartame | 2.75 |
| Acesulfame Potassium | 2.75 |
| Flavor Mentha Piperita | 2.50 |
| Color BQ Supra | 0.040 |
| Purified Water | q.s. |

Manufacturing Process

Nicotine polacrilex, flavoring solution, coloring solution and Critic acid solution were mixed with syrup preparation in mixing screw to obtain solid mass. The solid mass was passed through rope sizer and batch former to get lozenges. The lozenges were packed into strip pack/blister pack.

Example 5

Manufacturing Formula for Nicotine Lozenges 2 mg (with Maltitol)

| Ingredients | mg/tablet |
| --- | --- |
| Nicotine Polacrilex (20%) | 10.0 |
| Equivalent to Nicotine | 2.0 |

-continued

| Ingredients | mg/tablet |
| --- | --- |
| Citric Acid Monohydrate | 20.0 |
| Sucrose | 1597.0 |
| Maltitol Syrup | 1024.0 |
| Flavor Mentha Piperita | 2.50 |
| Color BQ Supra | 0.020 |
| Purified Water | q.s. |

Manufacturing Process

Nicotine polacrilex, flavoring solution, coloring solution and Critic acid solution were mixed with syrup preparation in mixing screw to obtain solid mass. The solid mass was passed through rope sizer and batch former to get lozenges. The lozenges were packed into strip pack/blister pack.

Example 6

Manufacturing Formula for Nicotine Lozenges 4 mg (with Maltitol)

| Ingredients | mg/tablet |
| --- | --- |
| Nicotine Polacrilex (20%) | 20.0 |
| Equivalent to Nicotine | 4.0 |
| Citric Acid Monohydrate | 20.0 |
| Sucrose | 1590.0 |
| Maltitol Syrup | 1020.0 |
| Flavor Mentha Piperita | 2.50 |
| Color BQ Supra | 0.040 |
| Purified Water | q.s. |

Manufacturing Process

Nicotine polacrilex, flavoring solution, coloring solution and Critic acid solution were mixed with syrup preparation in mixing screw to obtain solid mass. The solid mass was passed through rope sizer and batch former to get lozenges. The lozenges were packed into strips packs/blister pack.

Example 7

Manufacturing Process for Nicotine Lozenges 2 mg

1) Preparation of Flavoring Solution 1.83 kg of Mentha Piperita was passed through 200 mesh nylon cloth and was collected in a S.S container.

2) Preparation of Coloring Solution 14.65 g Color BQ Supra was added in warm purified water in S.S. vessel and was stirred for 5±1 mins. The color solution was passed through 200-mesh nylon cloth in a clean S.S. container.

3) Preparation of Citric Acid Solution 14.65 kg citric acid monohydrate was added in warm purified water in S.S. vessel and was stirred to obtain a clear solution.

4) Preparation of Sugar Syrup 1169.6 kg of sucrose, 750 kg of liquid glucose and purified water wad added and was set at temperature to NLT 93.3° C. to obtain syrup. The syrup was collected in stainless steeling holding tank.

5) Preparation of Lozenges 7.32 kg Nicotine polacrilex from powder feeder, flavoring solution of step 1, coloring solution of step 2, and citric acid solution of step 3 and added to sugar syrup of step 4 in mixing screw to form solid mass. The solid mass were transferred to rope sizer and batch former to obtain lozenges, which further passed through cooling tunnel.

6) Packaging of Lozenges

Lozenges obtained from step 5 were transferred to Sortomat DS and lozenges of desired size got separated from upper belt and rejected lozenges from lower belt. Lozenges were put in strips of paper/aluminum/barex/blister pack/strip pack/pillow pouch/twist pack/container pack.

Example 8

Manufacturing Process for Nicotine Lozenges 4 mg

1) Preparation of Flavoring Solution 1.83 kg of Mentha Piperita was passed through 200 mesh nylon cloth and was collected in a S.S container.

2) Preparation of Coloring Solution 29.30 g Color BQ Supra was added in warm purified water in S.S. vessel and was stirred for 5±1 mins. The color solution was passed through 200-mesh nylon cloth in a clean S.S. container.

3) Preparation of Citric Acid Solution 14.65 kg citric acid monohydrate was added in warm purified water in S.S. vessel and was stirred to obtain a clear solution.

4) Preparation of Sugar Syrup 1165.0 kg of sucrose, 747 kg of liquid glucose and purified water wad added and was set at temperature to NLT 93.3° C. to obtain syrup. The syrup was collected in stainless steeling holding tank.

5) Preparation of Lozenges 14.65 kg Nicotine polacrilex from powder feeder, flavoring solution of step 1, coloring solution of step 2, and citric acid solution of step 3 and added to sugar syrup of step 4 in mixing screw to form solid mass. The solid mass were transferred to rope sizer and batch former to obtain lozenges, which further passed through cooling tunnel.

6) Packaging of Lozenges

Lozenges obtained from step 5 were transferred to Sortomat DS and lozenges of desired size got separated from upper belt and rejected lozenges from lower belt. Lozenges were put in strips of paper/aluminum/barex/blister pack/strip pack/pillow pouch/twist pack/container pack.

Example 9

Comparison of Dissolution Profile of Commit 4 mg Lozenges and NICORETTE 4 mg Chewing Gum with Nicotine Lozenges of the Present Invention Dissolution profile was studied comparing in vitro study of COMMIT 4 mg lozenges and NICORETTE 4 mg chewing gums with nicotine lozenges (4 mg) of the present invention. The dissolution was carried using the following parameters.

Apparatus: USP Type 1 Basket
Medium: Phosphate Buffer pH 7.4
Volume: 900 ml
RPM: 100 rpm
Quantitative Analysis by HPLC Method The dissolution of nicotine lozenges (4 mg) of the present invention appears faster than that for the COMMIT 4 mg lozenges and NICORETTE 4 mg chewing gum.

It is to be understood that the above description is intended to be illustrative and not restrictive. Many embodiments will be apparent to those of skill in the art upon reviewing the above description. The scope of the invention should, therefore, be determined not with reference to the above description, but should instead to determined with reference to the appended claims, along with the full scope of equivalents to which such claims are entitled.

The invention claimed is:

1. A lozenge for transmucosal delivery consisting of 10 mg of nicotine polacrilex, 20 mg citric acid monohydrate, 1597 mg sucrose, 1024 mg liquid glucose, 2.5 mg mentha piperita, and a pharmaceutically acceptable coloring agent.

2. A lozenge for transmucosal delivery consisting of 20 mg of nicotine polacrilex, 20 mg citric acid monohydrate, 1590 mg sucrose, 1020 mg liquid glucose, 2.5 mg mentha piperita, and a pharmaceutically acceptable coloring agent.

3. A lozenge for transmucosal delivery consisting of 10 mg of nicotine polacrilex, 20 mg citric acid monohydrate, 1590 mg sucrose, 1020 mg maltitol syrup, 2.5 mg mentha piperita, and a pharmaceutically acceptable coloring agent.

4. A lozenge for transmucosal delivery consisting of 10 mg of nicotine polacrilex, 20 mg citric acid monohydrate, 1597 mg sucrose, 1024 mg maltitol syrup, 2.5 mg mentha piperita, and a pharmaceutically acceptable coloring agent.

5. A lozenge for transmucosal delivery consisting of 10 mg of nicotine polacrilex, 20 mg citric acid monohydrate, 2461.98 mg isomalt, 2.75 mg aspartame, 2.75 mg acesulfame potassium, 2.5 mg mentha piperita, and a pharmaceutically acceptable coloring agent.

6. A lozenge for transmucosal delivery consisting of 20 mg of nicotine polacrilex, 20 mg citric acid monohydrate, 2451.96 mg isomalt, 2.75 mg aspartame, 2.75 mg acesulfame potassium, 2.5 mg mentha piperita, and a pharmaceutically acceptable coloring agent.

7. A lozenge prepared by sizing a solid mass for transmucosal delivery consisting of (a) 10 mg of nicotine polacrilex, (b) 20 mg citric acid monohydrate, (c) a sugar syrup consisting of 1597 mg sucrose and 1024 mg liquid glucose, (d) 2.5 mg mentha piperita, and (e) a pharmaceutically acceptable coloring agent, wherein the lozenge provides single phase release of the nicotine.

8. A lozenge prepared by sizing a solid mass for transmucosal delivery consisting of (a) 10 or 20 mg of nicotine polacrilex, (b) 20 mg citric acid monohydrate, (c) a sugar syrup consisting of 1590 mg sucrose and 1020 mg liquid glucose, (d) 2.5 mg mentha piperita, and (e) a pharmaceutically acceptable coloring agent, wherein the lozenge provides single phase release of the nicotine.

* * * * *